United States Patent
Rondoni et al.

(10) Patent No.: US 11,437,150 B2
(45) Date of Patent: Sep. 6, 2022

(54) SYSTEM AND METHOD FOR SECURED SHARING OF MEDICAL DATA GENERATED BY A PATIENT MEDICAL DEVICE

(71) Applicant: Inspire Medical Systems, Inc., Golden Valley, MN (US)

(72) Inventors: John Rondoni, Plymouth, MN (US); David Todd Dieken, Minneapolis, MN (US)

(73) Assignee: Inspire Medical Systems, Inc., Golden Valley, MN (US)

( * ) Notice: Subject to any disclaimer, the term of this patent is extended or adjusted under 35 U.S.C. 154(b) by 295 days.

(21) Appl. No.: 16/419,486

(22) Filed: May 22, 2019

(65) Prior Publication Data

US 2019/0371479 A1 Dec. 5, 2019

Related U.S. Application Data

(60) Provisional application No. 62/678,640, filed on May 31, 2018.

(51) Int. Cl.
*G06F 12/14* (2006.01)
*H04L 29/06* (2006.01)
(Continued)

(52) U.S. Cl.
CPC ......... *G16H 80/00* (2018.01); *G06F 21/6245* (2013.01); *H04L 63/08* (2013.01); *H04L 63/10* (2013.01); *H04L 63/105* (2013.01)

(58) Field of Classification Search
CPC ......... H04L 41/28; H04L 63/10; H04L 63/08; H04L 9/32; G16H 80/00; G06F 21/6245
(Continued)

(56) References Cited

U.S. PATENT DOCUMENTS 7,039,810 B1 5/2006 Nichols
8,438,041 B2 5/2013 Green, III et al.
(Continued)

FOREIGN PATENT DOCUMENTS

WO 2017027729 2/2017
WO 2017083480 5/2017

OTHER PUBLICATIONS

International Search Report and Written Opinion dated Aug. 30, 2019.

*Primary Examiner* — Haresh N Patel
(74) *Attorney, Agent, or Firm* — Dicke, Billig & Czaja, PLLC

(57) ABSTRACT

Methods and systems provide for receiving, at a remote server, first data and a first sharing key acquired from a first processor associated with a first medical practice, and receiving, at the remote server, second data and a second sharing key acquired from a second processor associated with a second medical practice. The methods and systems provide for comparing, by the remote server, the first sharing key to the second sharing key, and granting, to the first and second processors by the remote server, access to the first and second data stored in the remote server in response to a successful comparison of the first and second sharing keys. The methods and systems provide for sharing, by the remote server, the first and second data with the first and second processors in response to the grant of access.

20 Claims, 10 Drawing Sheets

(51) Int. Cl.
*G16H 80/00* (2018.01)
*H04L 9/40* (2022.01)
*G06F 21/62* (2013.01)

(58) Field of Classification Search
USPC .......................................................... 726/4
See application file for complete search history.

(56) References Cited

U.S. PATENT DOCUMENTS

| | | | |
|---|---|---|---|
| 9,839,786 B2 | 12/2017 | Rondoni et al. | |
| 10,164,950 B2* | 12/2018 | Gross | G16H 40/67 |
| 2002/0082480 A1* | 6/2002 | Riff | G16H 40/67 |
| | | | 600/300 |
| 2002/0128860 A1 | 9/2002 | Leveque et al. | |
| 2003/0208465 A1 | 11/2003 | Yurko et al. | |
| 2005/0165623 A1 | 7/2005 | Landi et al. | |
| 2007/0050212 A1* | 3/2007 | Kearby | G16H 10/60 |
| | | | 705/3 |
| 2007/0253021 A1 | 11/2007 | Mehta et al. | |
| 2008/0088436 A1* | 4/2008 | Reeves | A61B 5/411 |
| | | | 340/539.12 |
| 2008/0091466 A1 | 4/2008 | Butler et al. | |
| 2008/0097550 A1* | 4/2008 | Dicks | A61B 5/0022 |
| | | | 607/59 |
| 2009/0193267 A1 | 7/2009 | Chung | |
| 2012/0277543 A1 | 11/2012 | Homchowdhury et al. | |
| 2014/0032242 A1 | 1/2014 | LaBorde et al. | |
| 2014/0088994 A1 | 3/2014 | Kroh | |
| 2015/0006201 A1 | 1/2015 | Pait et al. | |
| 2015/0067805 A1* | 3/2015 | Martin | H04L 67/1095 |
| | | | 726/7 |
| 2015/0199479 A1* | 7/2015 | Semen | G16H 10/60 |
| | | | 705/3 |
| 2015/0234984 A1* | 8/2015 | Singer | G06Q 40/08 |
| | | | 705/3 |
| 2016/0117448 A1 | 4/2016 | Van de Craen et al. | |
| 2016/0117471 A1* | 4/2016 | Belt | G16H 50/20 |
| | | | 705/2 |
| 2016/0193468 A1 | 7/2016 | Rondoni et al. | |
| 2016/0306929 A1 | 10/2016 | Butka et al. | |
| 2017/0116373 A1* | 4/2017 | Ginsburg | G16H 40/20 |
| 2017/0116375 A1* | 4/2017 | Kuwayama | G06F 21/6209 |
| 2017/0169186 A1* | 6/2017 | Tumma | G16H 10/60 |
| 2017/0237565 A1 | 8/2017 | Rommel | |
| 2019/0130127 A1* | 5/2019 | Bachmann | G06F 21/6245 |
| 2019/0348158 A1* | 11/2019 | Livesay | H04L 9/0891 |
| 2019/0355453 A1* | 11/2019 | Feigenwinter | G16H 10/60 |
| | | | 705/3 |

\* cited by examiner

*Figure 9*

SYSTEM AND METHOD FOR SECURED SHARING OF MEDICAL DATA GENERATED BY A PATIENT MEDICAL DEVICE

RELATED PATENT DOCUMENTS

This application claims the benefit of Provisional Patent Application Ser. No. 62/678,640 filed on May 31, 2018, to which priority is claimed pursuant to 35 U.S.C. § 119(e), and which is incorporated herein by reference in its entirety.

SUMMARY

Embodiments are directed to a method comprising receiving, at a remote server, first data and a first sharing key acquired from a first processor associated with a first medical practice, and receiving, at the remote server, second data and a second sharing key acquired from a second processor associated with a second medical practice. The method comprises comparing, by the remote server, the first sharing key to the second sharing key, and granting, to the first and second processors by the remote server, access to the first and second data stored in the remote server in response to a successful comparison of the first and second sharing keys. The method also comprises sharing, by the remote server, the first and second data with the first and second processors in response to the grant of access.

Embodiments are directed to a method comprising interrogating a patient medical device using a first processor associated with a first medical practice, and uploading, from the first processor to a remote server, first data and a first sharing key acquired from the patient medical device. The method comprises interrogating the patient medical device using a second processor associated with a second medical practice, and uploading, from the second processor to the remote server, second data and a second sharing key acquired from the patient medical device. The method also comprises comparing, by the remote server, the first sharing key to the second sharing key, and granting, to the first and second processors by the remote server, access to the first and second data stored in the remote server in response to a successful comparison of the first and second sharing keys. The method further comprises sharing, by the remote server, the first and second data with the first and second processors in response to the grant of access.

Embodiments are directed to a system comprising a remote server. The remote server comprises a communication interface configured to communicate with a first processor associated with a first medical practice and a second processor associated with a second medical practice. The remote server comprises memory configured to store first data and a first sharing key received from the first processor, and to store second data and a second sharing key received from the second processor. The remote server comprises a server processor coupled to the communication interface and the memory. The server processor is configured to compare the first sharing key to the second sharing key, grant, to the first and second processors, access to the first and second data stored in the remote server memory in response to a successful comparison of the first and second sharing keys, and share the first and second data with the first and second processors in response to the grant of access.

Embodiments are directed to a system comprising a first processor associated with a first medical practice and configured to interrogate a patient medical device to obtain first data and a first sharing key from the patient medical device. A second processor is associated with a second medical practice and configured to interrogate the patient medical device to obtain second data and a second sharing key from the patient medical device. A remote server is communicatively coupled to the first and second processors. The remote server is configured to receive the first data, the second data, the first sharing key, and the second sharing key respectively from the first and second processors in memory of the remote server, and compare the first sharing key to the second sharing key. The remote server is configured to grant, to the first and second processors, access to the first and second data stored in the remote server memory in response to a successful comparison of the first and second sharing keys, and share the first and second data with the first and second processors in response to the grant of access.

The above summary is not intended to describe each disclosed embodiment or every implementation of the present disclosure. The figures and the detailed description below more particularly exemplify illustrative embodiments

BRIEF DESCRIPTION OF THE DRAWINGS

Throughout the specification reference is made to the appended drawings, where like reference numerals designate like elements, and wherein:

FIG. 9 is an output produced by the system shown in FIG. 8 in accordance with various embodiments;

The figures are not necessarily to scale. Like numbers used in the figures refer to like components. However, it will be understood that the use of a number to refer to a component in a given figure is not intended to limit the component in another figure labeled with the same number.

DETAILED DESCRIPTION

In the following description, reference is made to the accompanying set of drawings that form a part of the description hereof and in which are shown by way of illustration several specific embodiments. It is to be understood that other embodiments are contemplated and may be made without departing from the scope of the present disclosure. The following detailed description, therefore, is not to be taken in a limiting sense.

Figure 1:
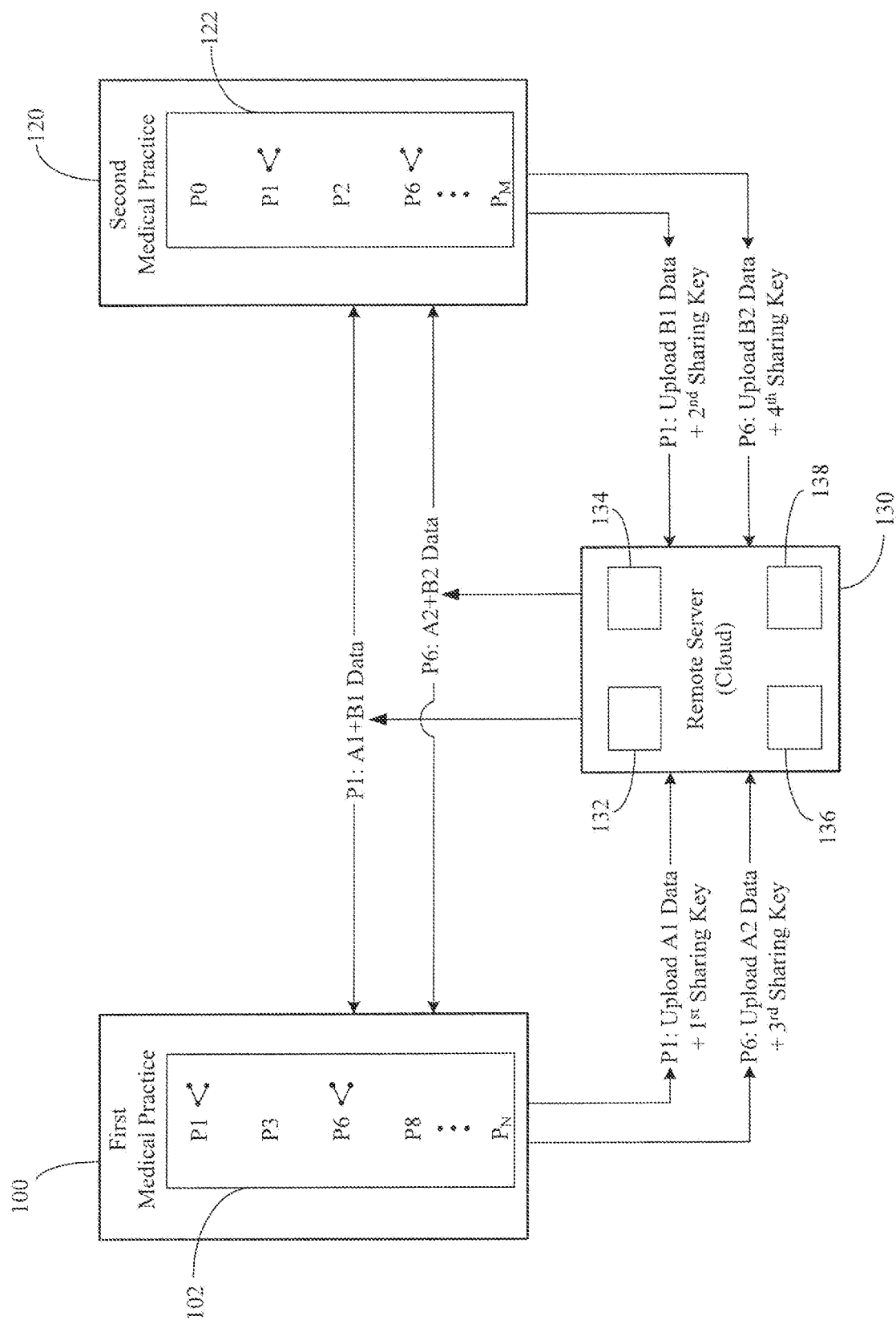
FIG. 1 illustrates a system for sharing medical data of a patient with different medical practices associated with the patient's care in accordance with various embodiments.

FIG. 1 illustrates a system for sharing medical data of a patient with different medical practices associated with the patient's care in accordance with various embodiments. FIG. 1 illustrates a scenario in which a number of different patients are cared for by a first medical practice 100 and a second medical practice 120. Typically, the first and second medical practices 100, 120 are legally unaffiliated. One or more clinicians are associated with each of the first and second medical practices 100, 120. The first medical practice 100 includes a first patient data system 102 which stores various types of information for each of the patients cared for by the first medical practice 100. The second medical practice 120 includes a second patient system 122 which stores various types of information for each of the patients cared for by the second medical practice 120.

In the representative example shown in FIG. 1, the first and second medical practices 100, 120 provide different medical services, although some of the services may be overlapping. For example, the first medical practice 100 can treat patients suffering from a sleep disorder, such as sleep apnea. The second medical practice 120 can treat patients suffering from cardiovascular disorders, such as pulmonary hypertension, high blood pressure, atrial fibrillation, heart failure, stroke, ischemic heart disease, and heart attack.

Among the many patients cared for by the first and second medical practices 100, 120, the two practices 100, 120 may care for the same patient. In the representative example shown in FIG. 1, patients P1 and P6 are cared for by both the first and second medical practices 100, 120. The quality of patient care can be significantly increased by sharing pertinent medical information about the patient with different physicians caring for the same patient. For example, it would be important for a cardiologist at the second medical practice 120 (e.g., a referring physician) to know that a particular patient suffering from cardiovascular disease and sleep apnea is being properly cared for by a sleep specialist at the first medical practice 100. Similarly, it would be important for a sleep specialist at the first medical practice 100 to know that this patient is being properly cared for by a cardiologist at the second medical practice 120.

Conventional approaches to sharing medical information for a patient cared for by different medical practices 100, 120 are antiquated, relying on sharing via a phone call, email, and facsimiles, for example. Shared patient data communicated via a phone call, email, and facsimiles cannot be readily integrated into the patient data system of the receiving medical practice. Moreover, any such medical information for a patient shared between different medical practices 100, 120 is typically limited in scope, such as to information relating to the most recent visit.

Embodiments of the disclosure are directed to systems and methods that provide for secured sharing of a patient's medical device data with different medical practices/clinicians associated with the patient's care. Various embodiments provide for automatic sharing of a patient's medical device data (also referred to herein as device data) with clinicians at different medical practices based on security information contained within the patient's medical device data acquired at the different medical practices. In addition to a patient's medical device data, patient data shared with different clinicians/medical practices can include one or both of clinician-generated data and patient-generated data. According to some embodiments, the shared data can include one or any combination of current, previous, and future medical device data associated with a patient. According to other embodiments, the shared data can include one or any combination of current, previous, and future clinician-generated data and/or patient-generated data, in addition to one or any combination of current, previous, and future medical device data associated with a patient. Embodiments of the disclosure provide for a patient's medical data to be easily shared and viewed by all clinicians/medical practices involved in the patient's care in a secured manner.

Referring again to FIG. 1, the first patient data system 102 is communicatively coupled to a remote server 130. The second patient data system 122 is also communicatively coupled to the remote server 130. The remote server 130 is typically a cloud data storage resource accessed via the Internet. In some embodiments, the remote server 130 can be a networked data storage resource accessed via private communication infrastructure. In the scenario shown in FIG. 1, a first subset of patient data acquired by and stored in the first patient data system 102 is communicated to and stored by the remote server 130. Similarly, a second subset of patient data acquired by and stored in the second patient data system 122 is communicated to and stored by the remote server 130. The first and second subsets of patient data represent data that, when shared by clinicians at the first and second medical practices 100, 120, can enhance care and treatment of a patient. Data that can enhance care and treatment of a patient is referred to herein as patient medical data. For example, the first and second subsets of patient data may exclude various types of patient data, such as insurance information and other patient data unrelated to the care and treatment of the patient.

The patient medical data communicated from the first patient data system 102 to the remote server 130 is stored in a first secured location 132 of the remote server 130. Similarly, the patient medical data communicated from the second patient data system 122 to the remote server 130 is stored in a second secured location 134 of the remote server 130. Initially, the patient medical data stored in the first secured location 132 is only accessible to a clinician associated with the first medical practice 100, and the patient data stored in the second secured location 134 is only accessible to a clinician associated with the second medical practice 120. As was discussed previously, patients P1 and P6 are cared for by both the first and second medical practices 100, 120, and it would be beneficial to facilitate sharing of patient medical data about patients P1 and P6 with clinicians at both the first and second medical practices 100, 120.

In the scenario shown in FIG. 1, at least some of the patients (e.g., P1 and P6) cared for by the first and second medical practices 100, 120 have been prescribed a patient medical device that generates data useful to the assessment and care of a patient by a clinician. In some embodiments, the patient medical device can be a device subject to medical regulatory body approval (e.g., FDA approval). In other embodiments, the patient medical device can be a consumer device, such as a wearable, which is not subject to medical regulatory body approval. The patient medical device can be an external medical device, an implantable medical device or a combination of external and implantable medical devices. In some embodiments, the patient medical device can be a diagnostic device capable of sensing and monitoring one or more physiologic signals or conditions of the patient. For example, a diagnostic device that generates patient medical data can be configured to sense and monitor one or more of oxygen saturation (e.g., via a pulse oximeter), sleep stage, respiration, snoring, posture (e.g., sleeping position, such as left, right, prone, supine), brain activity (e.g., electroencephalogram, EEG), muscle activity (e.g., electromyogram, EMG), glucose level, heart mechanical activity (e.g., heart sounds, seismocardiogram, SCG), heart electrical activity (electrocardiogram, ECG), heart rate, heart rate variability, blood pressure, temperature, and nerve activity. In other embodiments, the patient medical device can be a therapy delivery device capable of delivering a therapy to the patient. For example, a therapy delivery device that generates patient medical data can be an implantable pulse generator, neurostimulator, cardiac pacemaker, resynchronizer, cardioverter/defibrillator, drug administration device (e.g., drug pump, external or implantable), diaphragm stimulator, bladder stimulator, cochlear implant, hearing aid, muscle stimulator or other type of stimulation device. It is understood that a particular patient may be prescribed or recommended one or more patient medical devices, each of which can generate patient medical data.

In accordance with various embodiments, each patient medical device stores information that uniquely identifies the patient medical device, such as a serial number or other unique identifier. The information that uniquely identifies the patient medical device associated with the particular patient is referred to herein as a sharing key. When patient medical data is transmitted from the first and second patient data systems 102, 122 to the remote server 130, the patient medical data includes the sharing key of the patient medical device that generated the patient medical data. The remote server 130 processes sharing keys to facilitate automatic sharing of patient medical data between clinicians of different medical practices.

For example, and as shown in FIG. 1, A1 data is acquired from a patient medical device associated with patient P1 during a visit at the first medical practice 100. The A1 data is stored in the first patient data system 102 together with a first sharing key acquired from the patient medical device. B1 data is acquired from the same patient medical device associated with patient P1 during a visit at the second medical practice 120. The B1 data is stored in the second patient data system 122 together with a second sharing key acquired from the patient medical device. At some point in time, the A1 data and first sharing key are transmitted from the first patient data system 102 to the remote server 130 and stored in the secured location 132. At some point in time, the B1 data and second sharing key are transmitted from the second patient data system 122 to the remote server 130 and stored in the secured location 134.

The remote server 130 is configured to compare sharing keys of patient medical data stored at different secured locations in the remote server 130. For example, the remote server 130 is configured to compare the first sharing key of patient medical device stored at secured location 132 with the second sharing key of patient medical data stored at secured location 134. Because the first and second sharing keys originate from the same medical device of patient P1, the first sharing key is identical to the second sharing key. In response to the first sharing key matching the second sharing key, the remote server 130 is configured to grant to the first and second patient data systems 102, 122 access to the A1 and B1 data stored at secured locations 132, 134.

As is also in FIG. 1, A2 data is acquired from a patient medical device associated with patient P6 during a visit at the first medical practice 100. The A2 data is stored in the first patient data system 102 together with a third sharing key acquired from the patient medical device. B2 data is acquired from the same patient medical device associated with patient P6 during a visit at the second medical practice 120. The B2 data is stored in the second patient data system 122 together with a fourth sharing key acquired from the patient medical device. At some point in time, the A2 data and third sharing key are transmitted from the first patient data system 102 to the remote server 130 and stored in the secured location 136. At some point in time, the B2 data and fourth sharing key are transmitted from the second patient data system 122 to the remote server 130 and stored in the secured location 138.

The remote server 130 is configured to compare the third sharing key of the patient medical device stored at secured location 136 with the fourth sharing key of the patient medical data stored at secured location 138. Because the third and fourth sharing keys originate from the same medical device of patient P6, the third sharing key is identical to the fourth sharing key. In response to the third sharing key matching the fourth sharing key, the remote server 130 is configured to grant to the first and second patient data systems 102, 122 access to the A2 and B2 data stored at secured locations 136, 138.

According to various embodiments, the remote server 130 is configured to facilitate automatic sharing of a patient's medical data with different clinicians/medical practices associated with the patient's care in response to receiving patient medical data containing identical sharing keys from the different clinicians/medical practices. In some embodiments, the remote server 130 is configured to facilitate automatic sharing of a patient's past medical data, in addition to currently uploaded data, with different clinicians/medical practices associated with the patient's care in response to receiving patient medical data containing identical sharing keys from the different clinicians/medical practices. In further embodiments, the remote server 130 is configured to facilitate automatic sharing of a patient's past and future medical data, in addition to currently uploaded data, with different clinicians/medical practices associated with the patient's care in response to receiving patient medical data containing identical sharing keys from the different clinicians/medical practices.

Figure 2A:
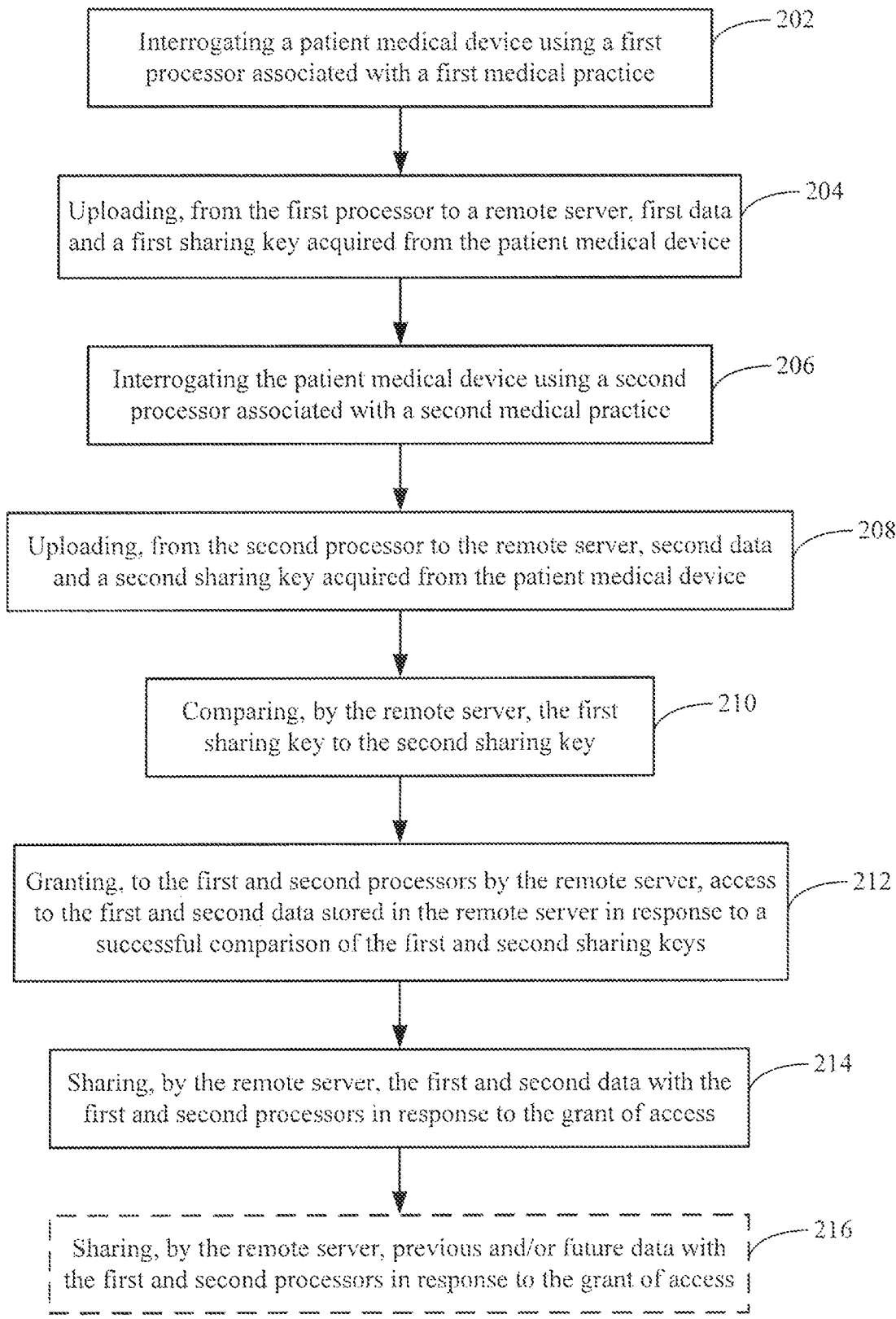
FIG. 2A illustrates a method of sharing patient medical data between different medical practices in accordance with various embodiments.

FIG. 2A illustrates a method of sharing patient medical data between different medical practices in accordance with various embodiments. The method shown in FIG. 2A involves interrogating 202 a patient medical device using a first processor associated with the first medical practice. The method involves uploading 204, from the first processor to a remote server, first data and a first sharing key acquired from the patient medical device. The method involves interrogating 206 the patient medical device using a second processor associated with the second medical practice. The method involves uploading 208, from the second processor to the remote server, second data and a second sharing key acquired from the patient medical device. The method also involves comparing 210, by the remote server, the first sharing key to the second sharing key. The method involves granting 212, to the first and second processors by the remote server, access to the first and second data stored in the remote server in response to a successful comparison of the first and second sharing keys. The method further involves sharing 214, by the remote server, the first and second data with the first and second processors in response to the grant of access. In some embodiments, the method involves sharing 216, by the remote server, previous and/or future data, in addition to the uploaded first and second data, with the first and second processors in response to the grant of access.

Figure 2B:
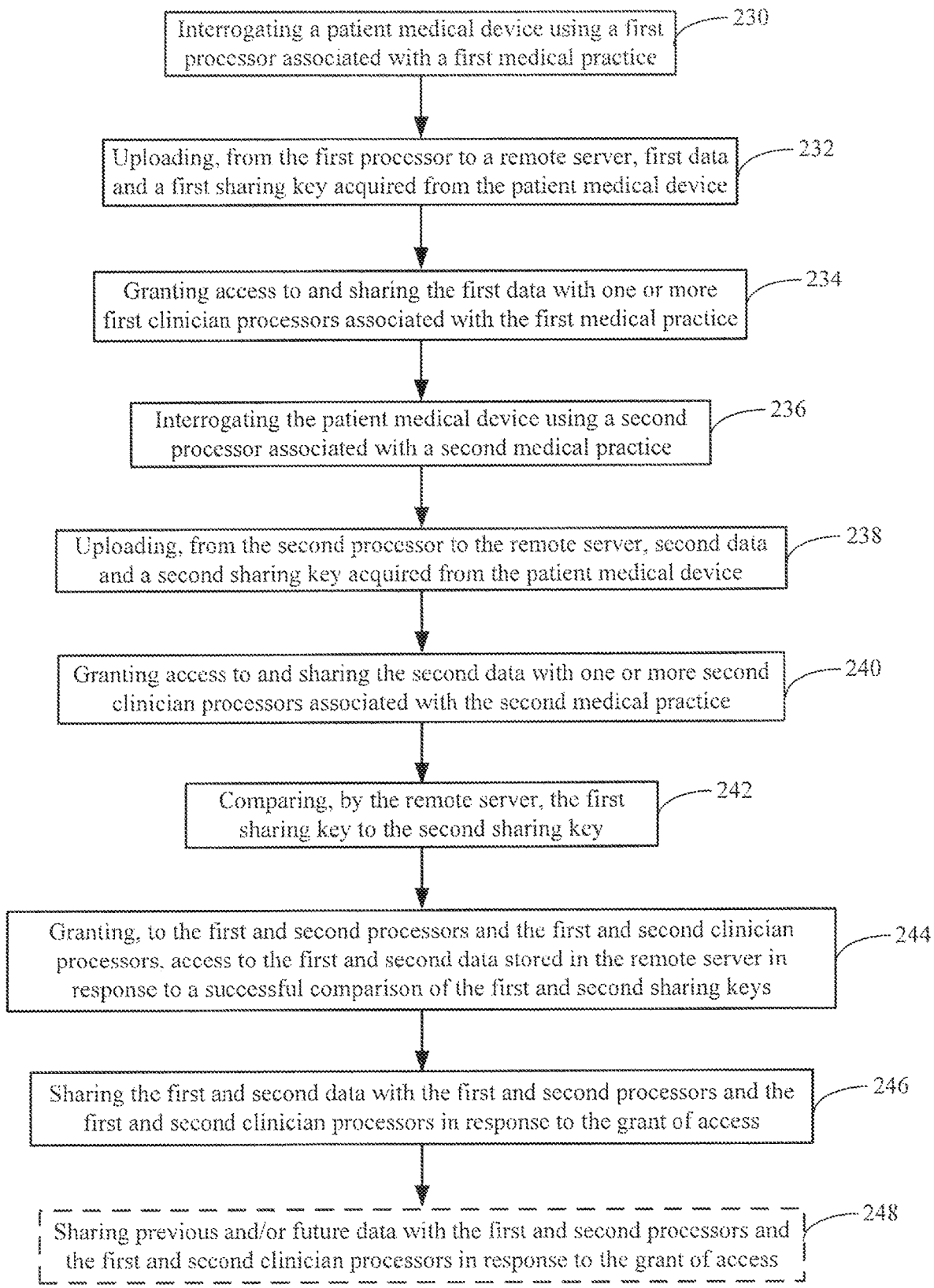
FIG. 2B illustrates a method of sharing patient medical data between different clinicians/medical practices in accordance with various embodiments.

FIG. 2B illustrates a method of sharing patient medical data between different clinicians/medical practices in accordance with various embodiments. Method shown in FIG. 2B involves interrogating 230 a patient medical device using a first processor associated with the first medical practice. The method involves uploading 232, from the first processor to a remote server, first data and a first sharing key acquired from the patient medical device. The method involves granting 234 access to and sharing the first data with one or more first clinician processors associated with the first medical practice. The method involves interrogating 236 the patient medical device using a second processor associated with the second medical practices. The method involves uploading 238, from the second processor to the remote server, second data and a second sharing key acquired from a patient medical device. The method involves granting 240 access to and sharing the second data with one or more second clinician processors associated with the second medical practices. The method also involves comparing 242, by the remote server, the first sharing key to the second sharing key. The method further involves granting, to the first and second processors and the first and second clinician processors, access to the first and second data stored in the remote server in response to a successful comparison of the first and second sharing keys. The method involves sharing 246 the first and second data with the first and second processors and the first and second clinician processors in response to the grant of access. The method may also involve sharing 248 previous and/or future data, in addition to the first and second data, with the first and second processors and the first and second clinician processors in response to the grant of access.

Figure 3:
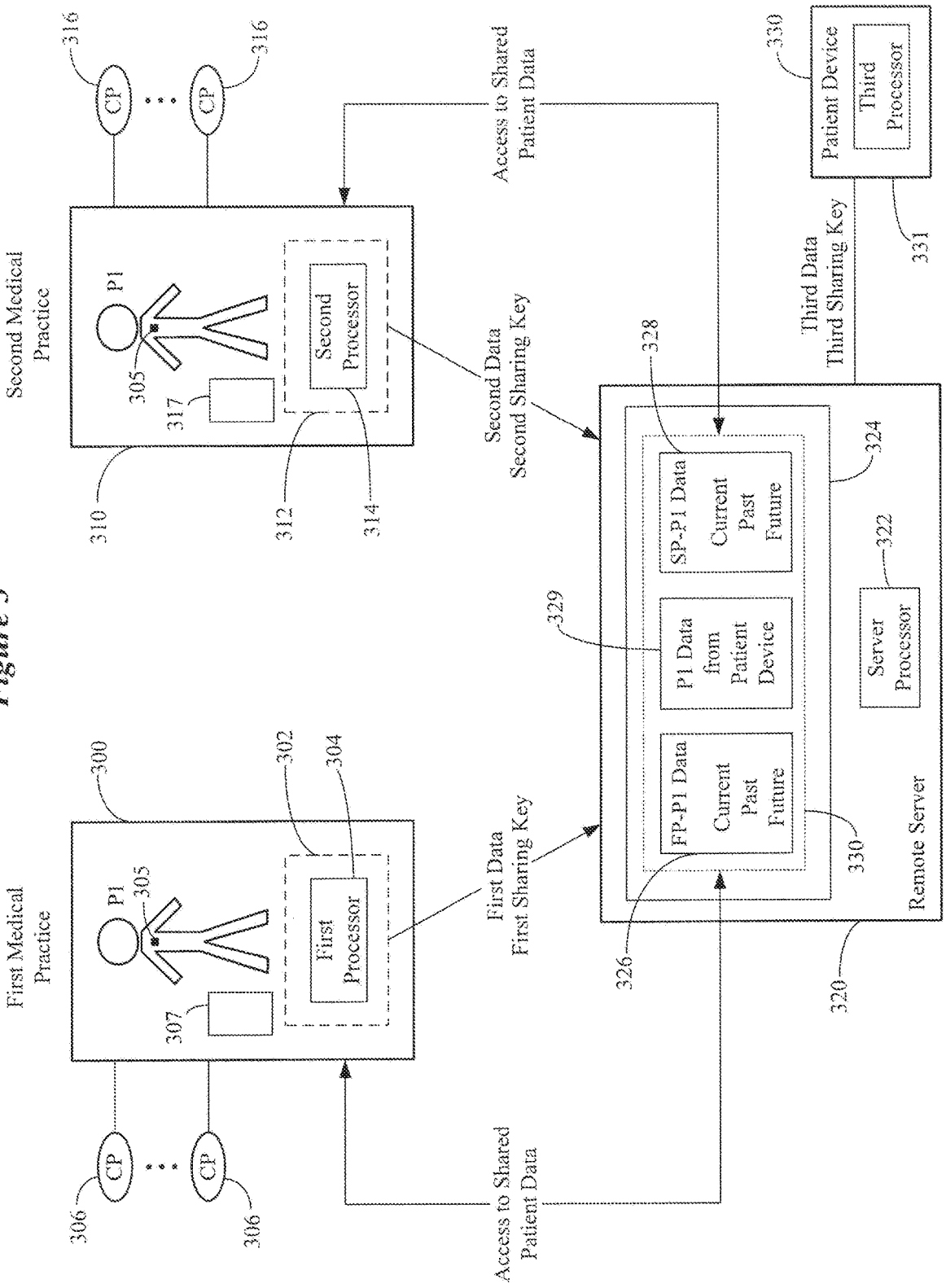
FIG. 3 illustrates a system for sharing medical data of a patient with different medical practices and clinicians associated with the patient's care in accordance with various embodiments.

FIG. 3 illustrates a system for sharing medical data of a patient with different medical practices and clinicians associated with the patient's care in accordance with various embodiments. FIG. 3 shows a patient P1 visiting a first medical practice 300 and, at a later time, visiting a second medical practice 310. The patient P1 is monitored by a patient medical device 305, which can be a diagnostic device, a therapy device, an external device or an implantable device, for example. During the patient's visit to the first medical practice 300, a first processor 304 of the medical system 302 is used to interrogate the patient medical device 305. The medical system 302 includes a communication interface (wired or wireless) that facilitates communication with and interrogation of the patient medical device 305. In some embodiments, the medical system 302 comprises a programmer with which a clinician can modify various programmable parameters (e.g., thresholds, diagnostic settings, therapy settings) of the patient medical device 305.

Using the first processor 304 of the medical system 302, first data and a first sharing key stored in the patient medical device 305 is transmitted (e.g., uploaded) to a memory resource of a patient data system 307 at the first medical practice 300. After the first data is transmitted to the patient data system 307, one or more first clinician processors 306 associated with the first medical practice 300 can access the patient data system 307 to view the first data. It is understood that the first clinician processors 306 can be a processor of a PC, tablet, phablet, smartphone or other digital assistant. In some embodiments, only a subset of the clinician processors 306 can be granted access to the first data based on pre-established criteria (e.g., to processors of clinicians having an email address ending in a specified domain name, such as @bridgewatersleep.com). For example, only specialists and clinicians with a predefined level of authorization may be granted access to the first data. At some point in time, the first data and the first sharing key acquired by the first processor 304 are uploaded to a secured location 326 in memory 324 of a remote server 320. In some embodiments, a user of the first processor 304 is authenticated prior to uploading the first data and the first sharing key to the remote server 320. In other embodiments, the first data and the first sharing key are encrypted such that only the remote server 320 can decrypt the first data.

In some embodiments, the secured location 326 stores the first data, which represents the current medical data most recently acquired from the patient medical device 305 at the first medical practice 300. In other embodiments, the secured location 326 stores past medical data that was previously acquired from the patient medical device 305 at the first medical practice 300, in addition to the current medical data. In further embodiments, the secured location 326 stores future medical data that, in the future, will be acquired from the patient medical device 305 at the first medical practice 300, in addition to the current medical data. In yet other embodiments, the secured location 326 stores current, past, and future medical data acquired from or to be acquired from the patient medical device 305 at the first medical practice 300.

According to some embodiments, a clinician at the first medical practice 300 can use a medical device (e.g., medical system 302) or a consumer device (e.g., clinician processor 306) to create clinician-generated information about patient P1. For example, the clinician can generate information about the patient's subjective health data. The clinician can generate information about the clinician's observations developed from data presented by the medical system 302 and/or from the patient visit. The clinician can generate information about the clinician's assessment of the patient's health/disease burden using data presented by the medical system 302 and/or developed from the patient visit. The clinician-generated information about patient P1 can be input to the patient data system 307 at the first medical practice 300, and uploaded to the secured location 326 in memory 324 of the remote server 320. In some embodiments, the clinician-generated information can be transmitted (e.g., uploaded) to the remote server 320 along with, or as part of, the first data. In other embodiments, the clinician-generated information can be separately input to the secured location 326 of the remote server 320, assuming the clinician has been granted access to the secured location 326.

In accordance with other embodiments, the patient P1 can use a medical device (e.g., medical system 302 or home medical system) or a consumer device (e.g., clinician processor 306 or home processor 330, such as a PC, tablet, phablet, or smartphone) to create patient-generated information. For example, the patient P1 can input information regarding the patient's subjective health, such as general wellness and specific parameters such as tiredness level. The patient P1 may also input answers to a questionnaire (e.g., Epworth Sleepiness Scale) and/or one or more open-ended questions. In some embodiments, the patient-generated information can be transmitted (e.g., uploaded) to the remote server 320 along with, or as part of, the first data. In other embodiments, the patient-generated information can be separately input to the secured location 326 of the remote server 320, assuming the patient has been granted access to the secured location 326.

FIG. 3 also shows the patient P1 visiting a second medical practice 310 at a time following the visit to the first medical practice 300. During the patient's visit to the second medical practice 310, a second processor 314 of the medical system 312 is used to interrogate the patient medical device 305. The medical system 312, which can be a programmer, includes a communication interface (wired or wireless) that facilitates communication with and interrogation of the patient medical device 305.

Using the second processor 314 of the medical system 312, second data and a second sharing key stored in the patient medical device 305 is transmitted to a memory resource of a patient data system 317 at the second medical practice 310. After the second data is transmitted to the patient data system 317, one or more second clinician processors 316 associated with the second medical practice 310 can access the patient data system 317 to view the second data. As was discussed previously, the second clinician processors 316 can be a processor of a PC, tablet, phablet, smartphone or other digital assistant. In some embodiments, only a subset of the clinician processors 316 can be granted access to the second data based on pre-established criteria. At some point in time, the second data and the second sharing key acquired by the second processor 314 are uploaded to a secured location 328 in memory 324 of the remote server 320. In some embodiments, a user of the second processor 314 is authenticated prior to uploading the second data and the second sharing key to the remote server 320. In other embodiments, the second data and the second sharing key are encrypted such that only the remote server 320 can decrypt the second data.

In some embodiments, the secured location 328 stores the second data, which represents the current medical data most recently acquired from the patient medical device 305 at the second medical practice 310. In other embodiments, the secured location 328 stores past medical data that was previously acquired from the patient medical device 305 at the second medical practice 310, in addition to the current medical data. In further embodiments, the secured location 328 stores future medical data that, in the future, will be acquired from the patient medical device 305 at the second medical practice 310, in addition to the current medical data. In yet other embodiments, the secured location 328 stores current, past, and future medical data acquired or to be acquired from the patient medical device 305 at the second medical practice 310.

According to some embodiments, a clinician at the second medical practice 310 can use a medical device (e.g., medical system 312) or a consumer device (e.g., clinician processor 316) to create clinician-generated information about patient P1 of a type previously described. The clinician-generated information about patient P1 can be input to the patient data system 317 at the second medical practice 310. In some embodiments, the clinician-generated information can be transmitted to the remote server 320 along with, or as part of, the second data. In other embodiments, the clinician-generated information can be separately input to the secured location 328 of the remote server 320, assuming the clinician has been granted access to the secured location 328.

In accordance with other embodiments, the patient P1 can use a medical device (e.g., medical system 312 or home medical system) or a consumer device (e.g., clinician processor 316 or home processor 330) to create patient-generated information of a type previously described. In some embodiments, the patient-generated information can be transmitted to the remote server 320 along with, or as part of, the second data. In other embodiments, the patient-generated information can be separately input to the secured location 328 of the remote server 320, assuming the patient has been granted access to the secured location 328.

The remote server 320 includes a server processor 322. The server processor 322 is configured to coordinate reception, processing, and transmission of patient medical data and, if applicable, clinician-generated information and patient-generated information. The server processor 322 is also configured to compare sharing keys associated with different patient medical data received from different medical practices and/or clinicians. For example, the server processor 322 compares the first sharing key associated with the first data stored in secured location 326 with the second sharing key associated with the second data stored in secured location 328.

In response to determining that the first sharing key matches the second sharing key, the server processor 322 may be configured to grant one or more specified entities access to the first and second data respectively stored in the first and second secured locations 326, 328 (depicted as combined secured location 330). For example, the server processor 322 may be configured to grant the first and second processors 304, 314 access to the first and second data respectively stored in the first and second secured locations 326, 328. The server processor 322 may be configured to grant the patient data systems 307, 317 access to the first and second data respectively stored in the first and second secured locations 326, 328. The server processor 322 may be configured to grant one or more of the clinician processors 306, 316 access to the first and second data respectively stored in the first and second secured locations 326, 328. The server processor 322 may be configured to grant the patient device 330 access to the first and second data respectively stored in the first and second secured locations 326, 328. The server processor 322 is configured to share the first and second data respectively stored in the first and second secured locations 326, 328 with the one or more entities in response to the grant of access.

According to some embodiments, data stored in the patient medical device 305 can be acquired by and transmitted from a processor at a location other than at a medical practice or clinician facility. For example, a processor 331 of a patient device 330 (e.g., a medical device or a consumer device such as a PC, tablet, phablet, smartphone) at the patient's home can be configured to interrogate the patient medical device 305 to acquire third data and a third sharing key. The third data and third sharing key are uploaded from the patient device 330 to a secured location 329 in memory 324 of the remote server 320. In some embodiments, the patient or patient's caregiver is authenticated prior to uploading the third data and the third sharing key to the remote server 320. In other embodiments, the third data and the third sharing key are encrypted such that only the remote server 320 can decrypt the third data.

The server processor 322 is configured to compare sharing keys stored secured locations 326, 328, and 329. In response to determining that the third sharing key matches the first and second sharing keys, the server processor 322 may be configured to grant one or more specified entities access to the first, second, and third data respectively stored in the first, second and third secured locations 326, 328, 329. For example, the server processor 322 may be configured to grant the first, second, and third processors 304, 314, 331 access to the first, second, and third data respectively stored in the first, second, and third secured location 326, 328, 329. One or more clinician processors 306, 316 may also be granted access to the first, second, and third data respectively stored in the first, second, and third secured location 326, 328, 329.

In various embodiments, patient-related data originating at the first medical practice 300 can only be shared with the second medical practice 310 in response to the remote server 320 receiving authorization from a clinician affiliated with the first medical practice 300. Similarly, patient-related data originating at the second medical practice 310 can only be shared with the first medical practice 300 in response to the remote server 320 receiving authorization from a clinician affiliated with the second medical practice 310. In some embodiments, patient-related data stored in the remote server 320 can only be shared with the first and second medical practices 300, 310 in response to the remote server 320 receiving authorization from the patient P1.

In some embodiments, previously granted access to patient-related data stored in the remote server 320 can be revoked by a clinician affiliated with the medical practice where the patient-related data originated. For example, the server processor 322 can be configured to revoke access by the second processor 314 to the first data in response to a revocation input received from a clinician of the first medical practice 300. Similarly, the server processor 322 can be configured to revoke access by the first processor 304 to the second data in response to a revocation input received from a clinician of the second medical practice 310. In some embodiments, the patient P1 can transmit a revocation input to the remote server 320 in order to revoke previously granted access by the first and/or second medical practices 300, 310 to patient P1's patient-related data stored in the remote server 320. Also, an upload notification can be generated by the remote server 320 to indicate successful receipt of patient-related data, including medical device data, clinician-generated data, and patient-generated data. The upload notification can be dispatched to the individual or persons that facilitated the data upload (e.g., a processor associated with one or more clinicians or a patient).

Figure 4:
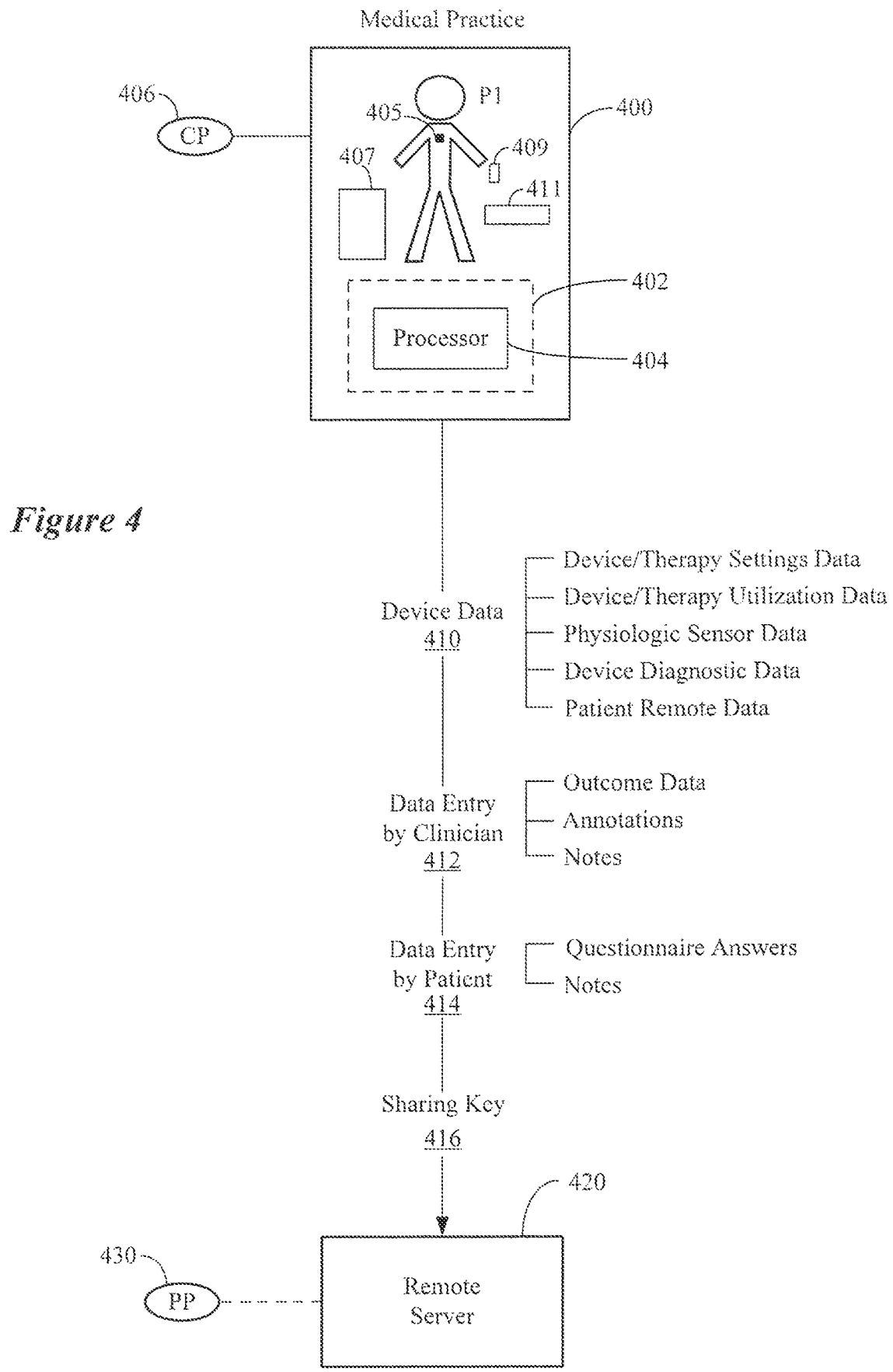
FIG. 4 illustrates various data that can be generated in connection with a patient visit to a medical practice and stored in a remote server in accordance with various embodiments.

FIG. 4 illustrates various data that can be generated in connection with a patient visit to a medical practice and stored in a remote server in accordance with various embodiments. The data shown in FIG. 4 represents data that can be generated by each of a number of different medical practices. As was discussed previously, a processor 404 of a medical system 402 associated with a medical practice 400 can interrogate a patient medical device 405 of a patient P1 to produce device data 410. The device data 410 is transmitted to the remote server 420 via the processor 404 or a processor of the patient medical system 407 associated with the medical practice 400.

The patient medical device 405 can be a diagnostic device or a therapy device. The device data 410 can include various types of data, including one or more of device/therapy settings data, device/therapy utilization data, physiologic sensor data, and device diagnostic data. For example, therapy settings data can include programmable parameter values unique to the patient, such as stimulation amplitude and electrode configuration. The therapy utilization data can include the date/time therapy was turned on, off, and paused; and patient configuration such as therapy amplitude. The physiologic sensor data can include data relevant to the treatment of a medical condition, such as AHI (Apnea Hypopnea Index), oxygen saturation, sleep stage, respiration, heart rate, heart rate variability, temperature, and blood pressure (or data produced by a diagnostic device discussed above). Device diagnostic data can include data used to determine if the patient medical device operation and/or performance is as expected or designed. Device diagnostic data can include, for example, battery status, electrode status, communication device status, processor status, memory status, firmware/software version/status, and pulse generator status.

In some embodiments, the patient medical device is a patient remote 409 configured to communicate with a therapy device 405, which may be implantable or external. The patient remote 409 can be configured to facilitate patient adjustment of one or more therapy settings of the therapy device 405 directly, without the need of programmer. The patient remote 409 includes a communication interface (wired or wireless) configured to facilitate communication with the therapy device 405. The patient remote 409 also includes memory that can store data produced by the therapy device 405, such as therapy settings data including patient-initiated programming changes, therapy utilization data, physiologic sensor data, and device diagnostic data. As such, the patient remote 409 can be interrogated by the processor 404 of the medical system 402 to produce the device data 410 rather than, or in addition to, interrogating the therapy device 405. In some embodiments, the patient remote 409 can be implemented to provide the functionality of the patient remote disclosed in commonly-owned U.S. Pat. No. 9,839,786 and Pat. Pub. No. 2016/0193468, each of which is incorporated herein by reference.

In other embodiments, the patient medical device is a programmer 411 configured to communicate with a therapy device 405, which may be implantable or external. The programmer 411 is configured to facilitate clinician adjustment of one or more therapy settings of the therapy device 405. The programmer 411 includes a communication interface (wired or wireless) configured to facilitate communication with the therapy device 405. The programmer 411 also includes memory that can store data produced by the therapy device 405, such as therapy settings data, therapy utilization data, physiologic sensor data, and device diagnostic data. The processor 404 that performs the interrogation of the therapy device 405 can be a processor of the programmer 411, which produces the device data 410. In some embodiments, the programmer 411 can be implemented to provide the functionality of the programmer disclosed in commonly-owned U.S. Pat. No. 9,839,786, which is incorporated herein by reference.

Clinician-generated information 412 can be transmitted to the remote server 420 via the processor 404, a processor of the patient medical system 407 associated with the medical practice 400, or a clinician processor 406. The clinician-generated information 412 can include outcome data, annotations, and/or notes generated by the clinician. The clinician-generated information 412 can also include responses to a single question or answers to a multi-part questionnaire. Clinician responses can be yes/no, numeric, slider, knob, a selection of predefined terms, or free text. Patient-generated information 414 can be transmitted to the remote server 420 via the processor 404, a processor of the patient medical system 407 associated with the medical practice 400, or a patient processor 430 (e.g., a home PC, tablet, phablet or smartphone). The patient-generated information 414 can include answers to a single question or a questionnaire, notes, and/or subjective health information. Patient-generated information 414 can include responses in the form of yes/no, numeric, slider, knob, a selection of predefined terms, or free text. A sharing key 416 is also transmitted from the processor 404 or a processor of the patient medical system 407 to the remote server 420.

Figure 5:
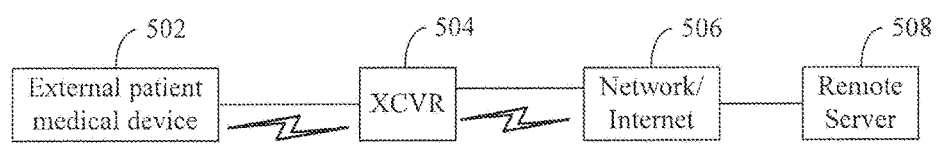
FIG. 5 shows a number of devices or systems that may be used to transmit data from a patient medical device to a remote server in accordance with various embodiments.

According to various embodiments, more than one device or system may be used to transmit data from a patient medical device to the remote server. For example, and with reference to FIG. 5, an external patient medical device 502 can communicate device data to a transceiver 504 via a wired or wireless link. The external patient medical device 502 can be implemented as a patient remote control, bedside communication device, bedside sensing device, wearable communication device, or wearable sensing device (e.g., pulse oximeter, blood pressure sensor, temperature sensor). The wired link can be a serial, parallel, USB, FireWire®, Lightning® or ISO/IEEE 11073 compliant link. The wireless link can be a Bluetooth® link, a ZigBee® link, WiFi®, IEEE 802.11 or ISO/IEEE 11073 compliant communication link. The transceiver 504 communicates the device data to a network and/or the Internet 506 via a wired and/or wireless communication link (e.g., GSM, CDMA, GPRS, HDSPA). The remote server 508 receives the device data from the network or the Internet 506. The devices/systems shown in FIG. 5 may be configured to forward the device data, or may store/forward the device data as connectivity permits.

Figure 6:
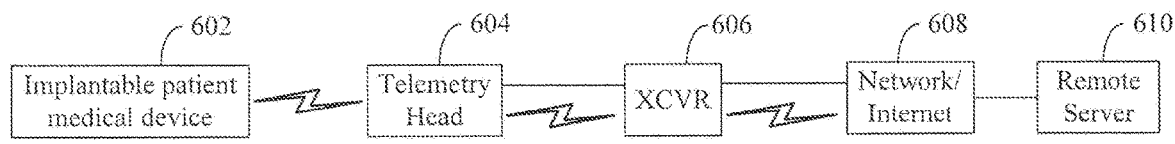
FIG. 6 shows a number of devices or systems that may be used to transmit data from a patient medical device to a remote server in accordance with various embodiments.

Referring to FIG. 6, an implantable patient medical device 602 can communicate device data to a telemetry head 604, which may be a near-field link (e.g., an inductive communication link or a far-field radiofrequency link). The implantable patient medical device 602 can be implemented as any implantable device, including those discussed herein. The device data is communicated from the telemetry head 604 to a transceiver 606, network/Internet 608, and remote server 610 in a manner discussed above. The devices/systems shown in FIG. 6 may be configured to forward the device data, or may store/forward the device data as connectivity permits.

Figure 7:
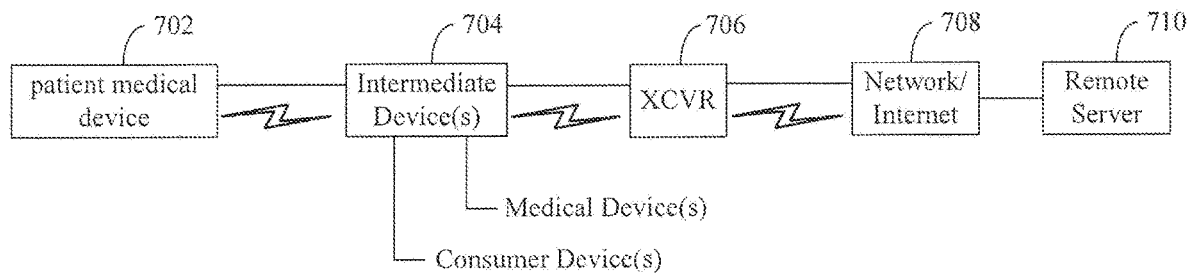
FIG. 7 shows a number of devices or systems that may be used to transmit data from a patient medical device to a remote server in accordance with various embodiments.

With reference to FIG. 7, a patient medical device 702 communicates device data to one or more intermediate devices 704 via a wired or wireless link. The patient medical device 702 can be an external or implantable device. The one or more intermediate devices 704 can include a medical device (e.g., patient remote, programmer), a consumer device (PC, laptop, tablet, phablet, smartphone), or a combination of medical and consumer devices. The device data acquired by the one or more intermediate devices 704 is communicated to a transceiver 706, network/Internet 708, and remote server 710 in a manner discussed above. The devices/systems shown in FIG. 7 may be configured to forward the device data, or may store/forward the device data as connectivity permits.

Figure 8:
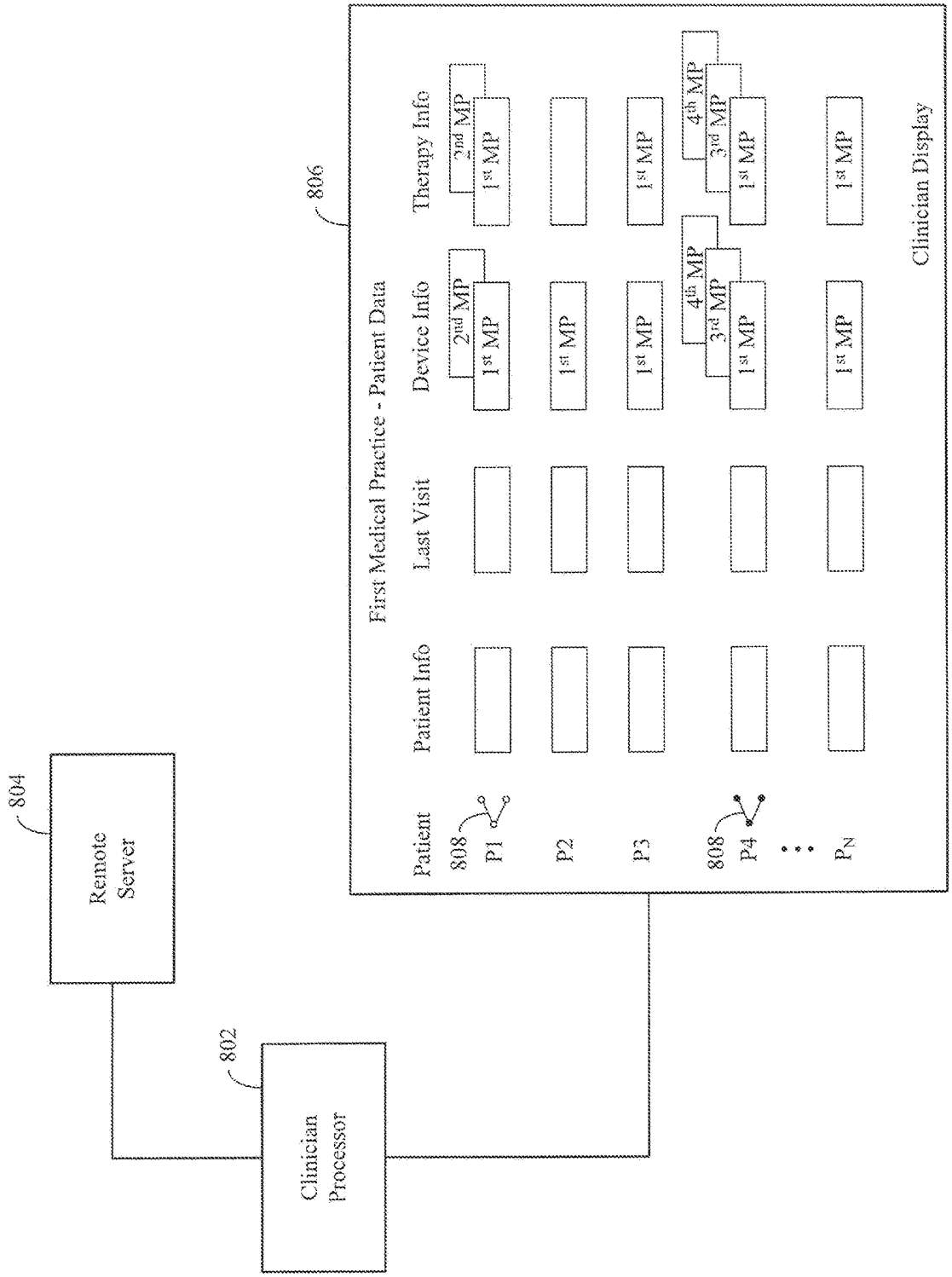
FIG. 8 illustrates a system for generating an output using patient-related data stored in a remote server in accordance with various embodiments.

FIG. 8 illustrates a system for generating an output using patient-related data stored in a remote server in accordance with various embodiments. The output may take various forms, including an electronic signal(s), a data file(s), displayed information, or printed information. In the illustrative embodiment shown in FIG. 8, the system is configured to provide viewing of patient data by a clinician of a first medical practice. For non-shared patients (e.g., patients cared for only by the first medical practice), the patient data viewable by a clinician and/or the patient can include aggregated data from multiple sources. For example, the patient data can include medical device data, clinician-generated data, and patient-generated data associated with care provided by a first medical practice. For shared patients (patients cared for by multiple medical practices), the patient data viewable by a clinician and/or the patient can include aggregated data from multiple sources and multiple medical practices. For example, the patient data can include medical device data, clinician-generated data, and patient-generated data associated with care provided by the first medical practice and a second medical practice (e.g., any number of medical practices).

In FIG. 8, a clinician processor 802 associated with the first medical practice is coupled to a remote server 804. The clinician processor 802 typically accesses the remote server 804 via a patient data system which stores various types of information for each of the patients cared for by the first medical practice. The remote server 804 shown in FIG. 8 contains the various data of the remote servers previously described with reference to FIGS. 1, 3 and 4. In particular, the remote server 804 includes various data about patients acquired from a multiplicity of medical practices using the secured processes previously discussed (e.g., use of sharing keys).

The clinician processor 802 is coupled to a display 806, which allows a clinician to view various types of data about patients cared for by the first medical practice. Presented on the display 806 is a summary of representative information about all patients associated with the first medical practice. In the illustrative example shown in FIG. 8, each patient is identified by a patient number (P1-$P_N$). Various data are associated with each patient number, including patient information, last visit, device information, and therapy information. In some embodiments, the patient information can include personal information about the patient, such as full legal name, date of birth, etc. In other embodiments, only a de-identified ID of the patient is presented. For some of the patients, information shared from another medical practice or clinician can be accessed and viewed on the clinician display 806. For example, patients P1 and P4 are cared for by one or more other medical practices in addition to the first medical practice. As such, patients P1 and P4 are considered shared patients. The shared status of patients P1 and P4 is graphically indicated by a share icon 808 positioned next to the patient number field or other field in a manner that that conspicuously identifies the patient as a shared patient. It can be seen that patients P2 and P3 do not have a shared icon, indicating that patients P2 and P3 are not shared patients. Instead, patients P2 and P3 are cared for only by the first medical practice or clinicians associated with the first medical practice.

In some embodiments, a characteristic of the shared icon 808 can change to convey information about a shared patient. For example, the share icon 802 associated with patient P1 includes 3 open circles, which can indicate when patient P1 first becomes a shared patient (e.g., denoting the first occurrence of patient data being received by the remote server 804 from another medical practice). The shared icon 802 associated with patient P4 includes 3 solid circles, which can indicate that new patient data for shared patient P4 has been received by the remote server 804. Other characteristics of the shared icon 802 can change to convey various information about a shared patient, such as a change in color, state (e.g., continuous or flashing) or configuration.

As was previously discussed, a patient medical device associated with a particular patient may be a diagnostic device (no therapy delivered) or a therapy device. For example, the patient medical devices associated with patients P1 P3 and P4 are therapy devices, whereas the patient medical device associated with patient P2 is a diagnostic device (hence no therapy information). The summary view presented on the clinician display 806 indicates that the device information and therapy information for patient P1 includes information acquired from both the first medical practice and a second medical practice. The summary view also indicates that the device information and therapy information for patient P4 includes information acquired from the first, third, and fourth medical practices. In some embodiments, clicking on a device information tab associated with patient P1 or P4 can provide detailed device information acquired by the different medical practices. The device information can include physiologic sensor information, device diagnostics data, and other information regarding the operation and status of the patient medical devices associated with patients P1 and P4. In some embodiments, clicking on a therapy information tab associated with patient P1 or P4 can provide detailed therapy information acquired by the different medical practices. The therapy information can include therapy settings data, therapy utilization data, and sensor data, for example.

Although not shown in FIG. 8, the data presented on the display 806 can include one or both of clinician-generated data and patient-generated data. In the case of non-shared patients, the clinician-generated data and patient-generated data is associated with care provided only by the first medical practice. In the case of shared patients, the clinician-generated data and patient-generated data is associated with care provided by multiple medical practices.

Figure 9:
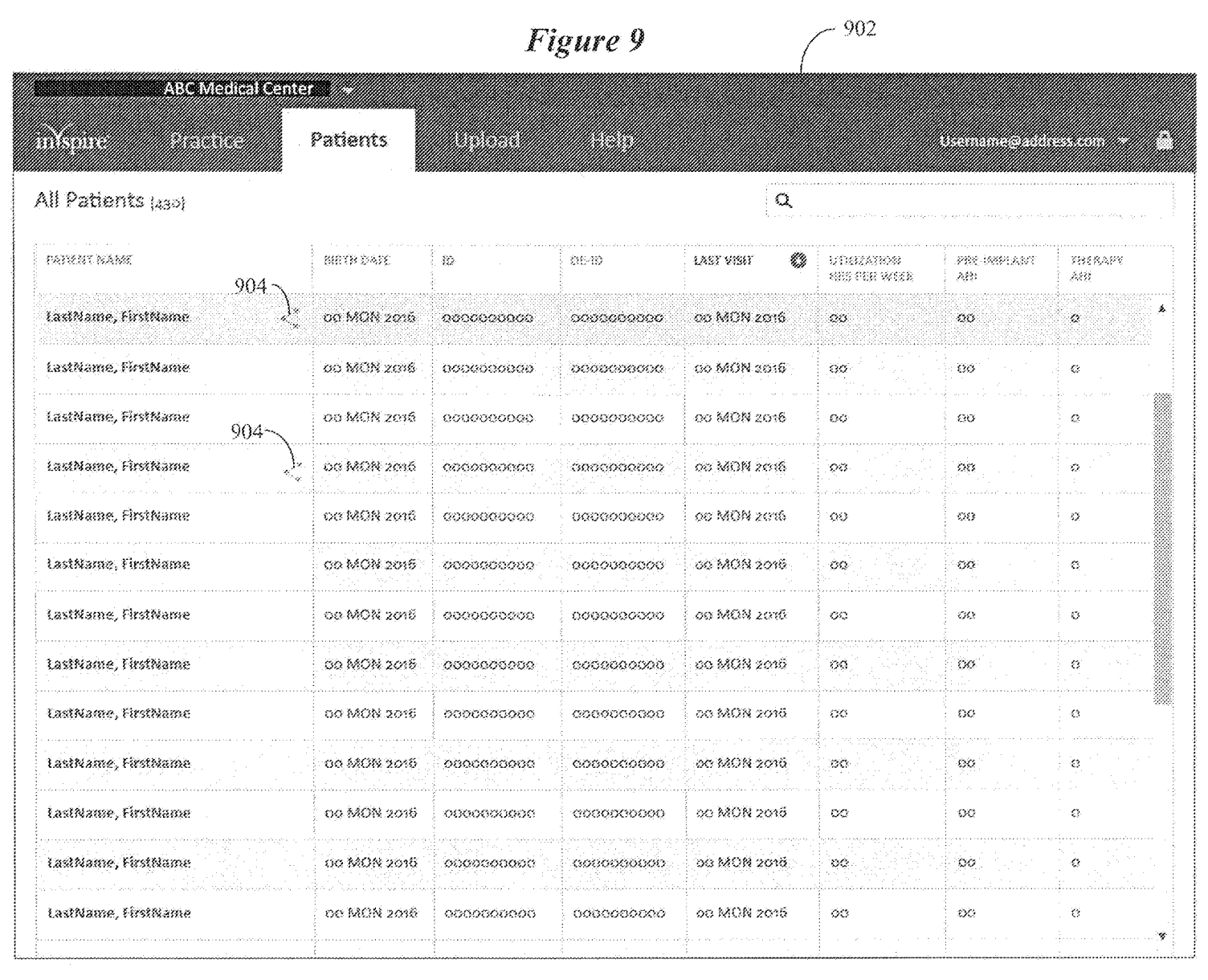

FIG. 9 is an output produced by the system shown in FIG. 8 in accordance with various embodiments. The output shown in FIG. 9 represents information presented on a display or a printed report for 13 different patients. Two of the patients are shared patients, each of which is identified graphically by a share icon 904. Identification, personal, and last visit information is presented for each of the patients. In this illustrative example, various therapy information is presented for the patients, each of whom has an implanted neurostimulation device configured to deliver a neurostimulation therapy for treating an obstructive disordered breathing condition. The therapy information includes utilization data (usage in hours per week), pre-implant AHI, and therapy (titrated) AHI.

Figure 10:
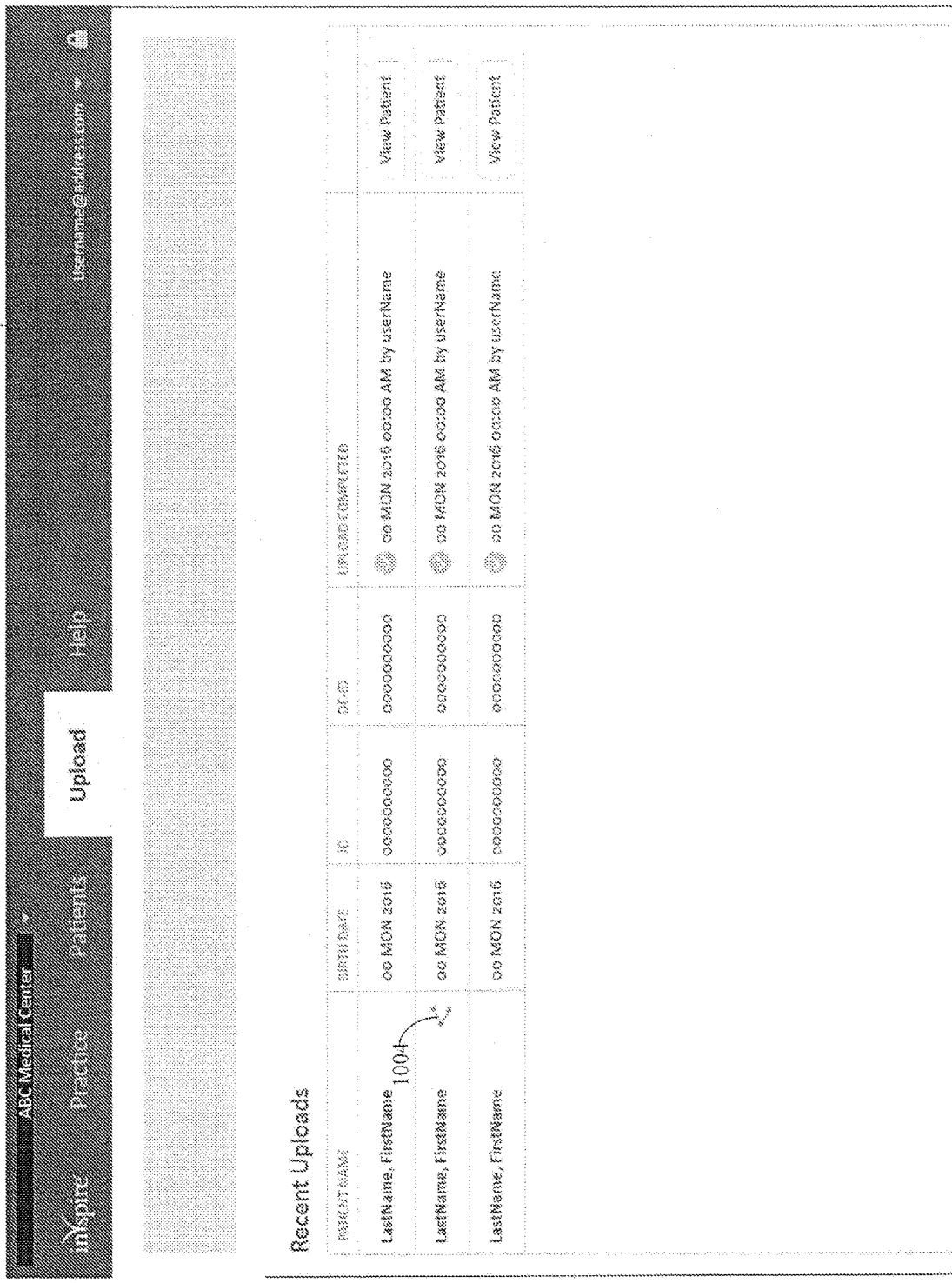
FIG. 10 shows an upload screen presented on a display of a medical device or a consumer device configured to upload patient-related information to a remote server in accordance with various embodiments.

FIG. 10 shows an upload screen presented on a display of a medical device or a consumer device configured to upload patient-related information to a remote server in accordance with various embodiments. In this illustrative example, the upload screen 1002 shows recent uploads for three different patients transmitted from a first medical practice (ABC Medical Center) to a remote server. The second patient shown in the upload screen 1002 is a shared patient, as indicated by the share icon 1004. The share icon 1004 provides a clear indication that the recently uploaded patient-related information for the second patient will be accessible and viewable by one or more medical practices in addition to the first medical practice.

Figure 11:
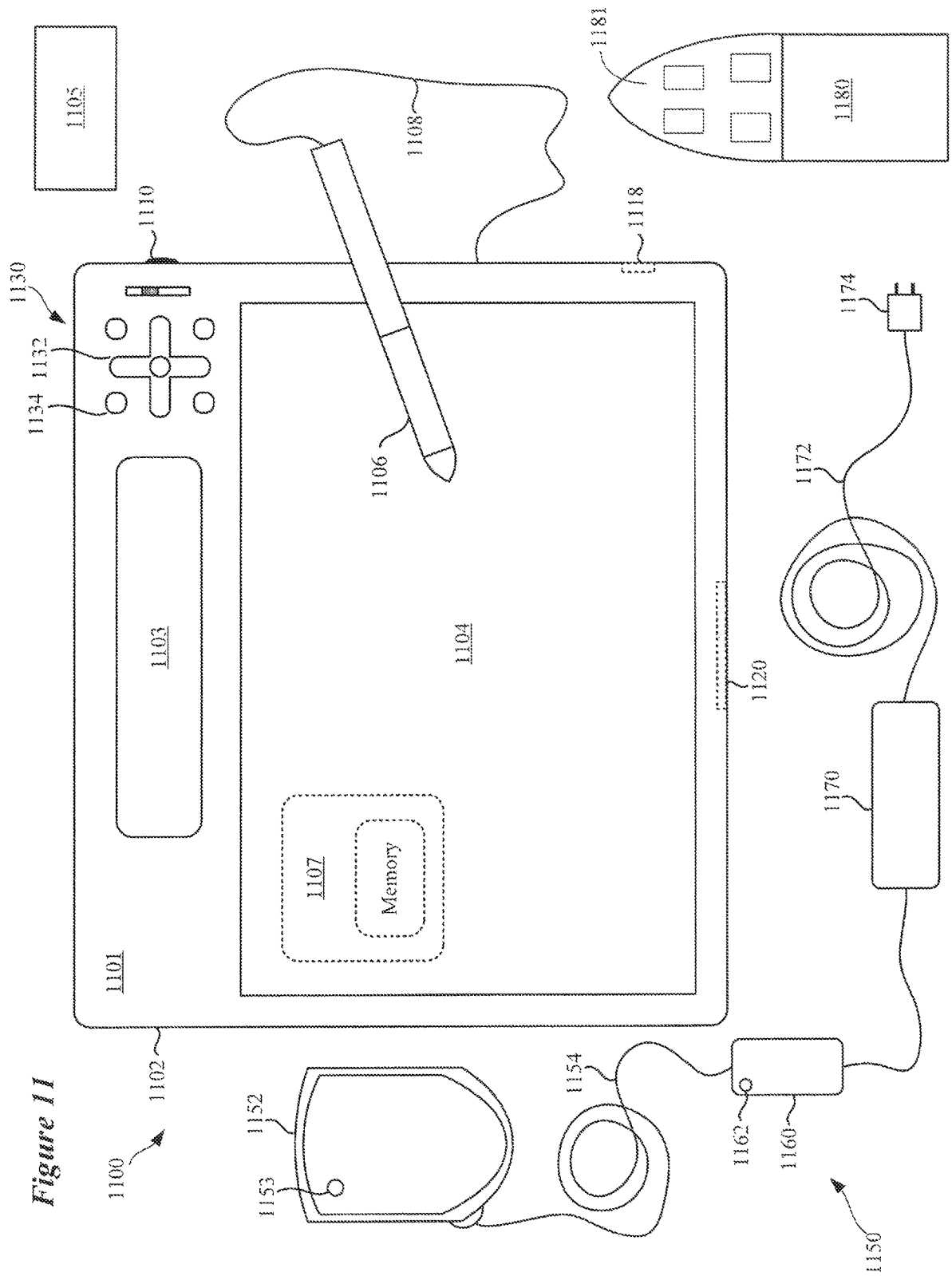
FIG. 11 shows a representative wireless programmer configured to communicate with an implantable patient therapy device in accordance with various embodiments.

FIG. 11 shows a medical system/device that can be used at a medical practice to generate patient medical data that can be uploaded to a remote server in accordance with various embodiments. FIG. 11 shows a wireless programmer 1102 configured to communicate with a patient medical device 1105 via a telemetry cable 1150. According to various embodiments, the wireless programmer 1102 can be implemented as a tablet computer or other mobile computing device (e.g., a phablet, notebook or laptop). The wireless programmer 1102 is configured to implement an application (also referred to as an "app") or a browser that facilitates clinician interaction with the telemetry cable 1150 and the patient medical device 1105. In some embodiments, the patient medical device 1105 is a neurostimulation device configured to deliver a neurostimulation therapy for treating an obstructive disordered breathing condition of the patient.

In such embodiments, the neurostimulation device 1105 includes a neurostimulator and a stimulation lead that extends from the housing of the neurostimulator to the hypoglossal nerve in the patient's neck. A sensing lead extends from the housing of the neurostimulator and is implanted at an intercostal muscle location of the rib cage. The sensing lead detects intercostal muscle movement during patient respiration, signals from which are used to detect patient respiration. A pulse generator in the neurostimulator provides electrical stimulation to the hypoglossal nerve via the stimulation lead based on detected patient respiration.

The wireless programmer 1102 can be used by a clinician to interrogate the patient medical device 1105 and make adjustments to various parameters (referred to as "programming"), monitor therapy delivered by the patient medical device 1105, and monitor patient adherence to prescribed therapy. FIG. 11 also shows a wireless patient remote 1180 configured to facilitate patient adjustment of one or more therapy settings of the patient medical device 1105 directly (i.e., without the need of programmer 1102).

The telemetry cable 1150 communicates wirelessly with the patient medical device 1105 and facilitates wireless communication between the patient medical device 1105 and the wireless programmer 1102. The wireless programmer 1102 includes a display 1104 and a stylus 1106 which allows the clinician to interact with the display 1104, such as by inputting, modifying, and reviewing data. In some embodiments, the display 1104 can be configured as a touchscreen, in which case the stylus 1106 may be excluded or an optional accessory. The wireless programmer 1102 includes a number of interfaces, buttons, and controls, several of which are shown in the illustrative embodiment of FIG. 11. A power button 1110 is provided on an upper right edge of the housing 1101, and a cluster of controls 1130 is provided on an upper right portion of the front surface of the housing 1102. The control cluster 1130 includes a multi-position control 1132 that allows the clinician to interact with a processor 1107 and display 1104 of the programmer 1102 in various ways. The processor 1107 of the programmer 1102 can be programmed to implement the various processes and functions described herein. Additional buttons 1134 can be situated proximate (or apart from) the control cluster 1130. The wireless programmer 1102 includes a number of different interfaces/components including a power connector plus USB port 1118 and a network cable and USB port 1120. The interfaces and components listed above are for purposes of illustration, not of limitation.

The telemetry cable 1150 is configured to wirelessly communicate with both the wireless programmer 1102 and the patient medical device 1105. The telemetry cable 1150 effectively serves as a wireless bridge or modem between the programmer 1102 and the patient medical device 1105. In accordance with the embodiment shown in FIG. 11, the telemetry cable 1150 includes a telemetry head 1152 configured to wirelessly communicate with the patient medical device 1105 via a near-field link. The telemetry head 1152 is shown to include a status indicator 1153, such as an LED indicator. In some embodiments, the telemetry head 1152 is configured to inductively communicate with the patient medical device 1105 via a near-field link.

A cable 1154 extends from the telemetry head 1152 and is connected to a wireless transceiver 1160. The wireless transceiver 1160 may be configured for short-range radio frequency (RF) communication. For example, the wireless transceiver 1160 may be configured to implement a short-range RF communication link, such as by implementing a Bluetooth® or ZigBee® communications protocol. In some embodiments, the wireless transceiver 1160 can be configured to wirelessly communicate with existing network infrastructure via an appropriate RF communication protocol, such as Wi-Fi®. The wireless transceiver 1160 is shown to include a status indicator 1162. Power is supplied to the telemetry cable 1150 by way of a power supply 1170, which is shown to include a power cable 1172 terminated by a standard AC wall plug 1174. The power supply 1170 provides power for both the wireless transceiver 1160 and the telemetry head 1152.

The patient remote 1180 (patient remote) is shown to include buttons to allow the patient to modify therapy parameters, and status indicators for implantable device status (e.g., remote and implantable device communication status and implantable device battery status) and remote status (remote battery status). The patient remote 1180 is utilized by a patient during home use of the therapy and to make necessary adjustments of therapy parameters (e.g., stimulation amplitude) if needed or desired. The patient remote 1180 shown in FIG. 11 has a control panel 1181 which includes a number of user actuatable control buttons. The control buttons provided on the control panel 1181 allow the patient to turn therapy on and off, pause therapy, and allow the patient to adjust one or more parameters that affect the operation of the implantable medical device that is surgically implanted in the patient. For example, the control panel 1181 can include a therapy ON button and a therapy OFF button, which can be actuated to respectively turn on and off stimulation therapy by the patient. An increase control provided on the control panel 1181 allows the patient to increase stimulation strength within a range selected by the clinician. A decrease control provided on the control panel 1181 allows the patient to decrease the stimulation strength within a range pre-selected by the clinician.

The wireless programmer 1102, patient remote 1180, and patient medical device 1105 (e.g., a neurostimulator) can be implemented in accordance with commonly-owned U.S. Pat. No. 9,839,786 (Rondoni et al.) and U.S. Pat. Pub. No. 2016/0193468 (Rondoni et al.), each of which is incorporated herein by reference.

The term patient medical device as used herein is intended to represent a broad range of external and implantable devices. A patient medical device can be a device subject to medical regulatory body approval or a consumer device, such as a wearable, which is not subject to medical regulatory body approval. A patient medical device can be a device configured to communicate with an implantable therapy or a diagnostic device (e.g., a patient remote or programmer). A patient medical device can be a device in a patient's home, bedroom, at a medical clinic, a clinician device, a wearable device, a portable device, a stationary device or an implantable device.

In this disclosure, reference is made to various processors (e.g., first, second, third, server, clinician processors). A processor as disclosed herein may be a single processor or multiple processors. A processor can be implemented as one or more of a multi-core processor, a digital signal processor (DSP), a microprocessor, a programmable controller, a general-purpose computer, a special-purpose computer, a hardware controller, a software controller, a combined hardware and software device, such as a programmable logic controller, a programmable logic device (e.g., FPGA, ASIC), a personal computer (PC), a main frame computer, a laptop, a notebook, a tablet, a phablet, a personal digital assistant, or a smartphone. A processor can include or be coupled to memory, such as RAM, SRAM, ROM, flash, SSD (solid-state drive), or a hard drive (HDD). A processor can be a component of a computing or communication device that cooperates with a communication interface (e.g., wired or wireless interface), a display (e.g., a touch screen), memory (RAM, ROM, flash, SSD, hard drive), and a user interface (e.g., keyboard, mouse, voice control interface, touch screen). A processor can include or be coupled to one or more communication interfaces, such as a wired and/or wireless interface (e.g., USB, FireWire®, Lightning®, GSM, CDMA, GPRS, HDSPA, Bluetooth®, ZigBee®, IEEE 802.11, ISO/IEEE 11073 compliant interface). A processor of the present disclosure can be programmed to execute program instructions or code (e.g., software, firmware) to cause the processor to perform the processes disclosed herein, such as those described with reference to the Figures (e.g., interrogation, uploading, transmitting, comparing, authenticating, granting, sharing, revoking, encrypting).

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof

What is claimed is:

1. A method, comprising:
   interrogating a patient medical device using a first processor associated with a first medical practice;
   uploading, from the first processor to a remote server, first data and a first sharing key acquired from the patient medical device;
   interrogating the patient medical device using a second processor associated with a second medical practice;
   uploading, from the second processor to the remote server, second data and a second sharing key acquired from the patient medical device;
   comparing, by the remote server, the first sharing key to the second sharing key;
   granting, to the first and second processors by the remote server, access to the first and second data stored in the remote server in response to a successful comparison of the first and second sharing keys;
   automatically sharing, by the remote server, the first and second data with both of the first and second processors in response to the grant of access; and
   following the step of sharing, prompting a display associated with the first processor to display a shared icon indicating that a patient assigned to the patient medical device is being cared for by both of the first and second medical practices.

2. A method, comprising:
   interrogating a patient medical device using a first processor associated with a first medical practice wherein the first processor is part of a first patient system of the first medical practice and which stores various types of information for patients cared for by the first medical practice;
   uploading, from the first processor to a remote server, first data and a first sharing key acquired from the patient medical device to a first location of a memory of the remote server;
   interrogating the patient medical device using a second processor associated with a second medical practices, wherein the second processor is part of a second patient system of the second medical and which stores various types of information for patients cared for by the second medical practice;

uploading, from the second processor to the remote server, second data and a second sharing key acquired from the patient medical device to a second location of the memory of the remote server, the second location being different from the first location;

wherein the first and second medical practices are legally unaffiliated such that the first patient system is distinct from and unavailable to the second patient system;

comparing, by the remote server, the first sharing key to the second sharing key;

granting, to the first and second processors by the remote server, access to the first and second data stored in the remote server in response to a successful comparison of the first and second sharing keys by the remote server as part of the step of comparing; and automatically sharing, by the remote server, the first and second data with both of the first and second processors in response to the grant of access during the step of granting.

3. The method of claim 2, comprising, in response to the successful comparison of the first and second sharing keys:
granting, to the first and second processors by the remote server, access to previous data uploaded by the first and second processors to the remote server; and
sharing, by the remote server, the first data, the second data, and the previous data with the first and second processors in response to the grant of access.

4. The method of claim 2, comprising, in response to the successful comparison of the first and second sharing keys:
granting, to the first and second processors by the remote server, access to future data uploaded by the first and second processors to the remote server; and
sharing, by the remote server, the first data, the second data, and the future data with the first and second processors in response to the grant of access.

5. The method of claim 2, wherein the first sharing key is the same as the second sharing key.

6. The method of claim 2, wherein the first and second sharing keys comprise information that uniquely identifies the patient medical device.

7. The method of claim 2, wherein the first and second sharing keys comprise a serial number of the patient medical device.

8. The method of claim 2, wherein:
one or more first clinician processors are associated with the first medical practice;
in response to uploading the first data and the first sharing key from the first processor to the remote server, the remote server grants access to and shares the first data with the one or more first clinician processors;
one or more second clinician processors are associated with the second medical practice; and
in response to uploading the second data and the second sharing key from the second processor to the remote server, the remote server grants access to and shares the second data with the one or more second clinician processors.

9. The method of claim 8, wherein:
the remote server grants access to and shares the first data only with a subset of the one or more first clinician processors; and
the remote server grants access to and shares the second data only with a subset of the one or more second clinician processors.

10. The method of claim 8, comprising, in response to the successful comparison of the first and second sharing keys:
granting, to the respective one or more first and second clinician processors by the remote server, access to one or both of previous and future data uploaded by the first and second processors to the remote server; and
sharing, by the remote server, the first data, the second data, and one or both of the previous data and the future data with the respective one or more first and second clinician processors in response to the grant of access.

11. The method of claim 2, wherein the first and second data comprise one or more of medical device settings data, medical device utilization data, physiologic sensor data, and medical device diagnostic data.

12. The method of claim 2, wherein the first and second data comprises one or both of clinician generated information and patient generated information.

13. The method of claim 2, comprising:
authenticating a first user of the first processor prior to uploading the first data and the first sharing key from the first processor to the remote server; and
authenticating a second user of the second processor prior to uploading the second data and the second sharing key from the second processor to the remote server.

14. The method of claim 2, wherein the first and second data and the first and second sharing keys are encrypted such that only the remote server can decrypt the first and second data and the first and second sharing keys.

15. The method of claim 2, comprising:
interrogating the patient medical device using a third processor at a location distinct from the first and second medical practices;
uploading, to the remote server, third data and a third sharing key acquired from the patient medical device interrogation at the distinct location;
comparing, by the remote server, the third sharing key to the first and second sharing keys;
granting, to the first, second, and third processors by the remote server, access to the first, second, and third data stored in the remote server in response to a successful comparison of the first, second, and third sharing keys; and
sharing, by the remote server, the first, second, and third data with the first, second, and third processors in response to the grant of access.

16. The method of claim 2, wherein the step of granting includes simultaneously granting access to the first and second processors by the remote server to the first and second data stored in the remote server in response to a successful comparison of the first and second sharing keys.

17. The method of claim 2, further comprising:
following the step of sharing, prompting a display associated with the first processor to display a shared icon indicating that a patient assigned to the patient medical device is being cared for by both of the first and second medical practices.

18. The method of claim 2, wherein the patient medical device includes a pulse generator implanted within the patient.

19. A method, comprising:
receiving, at a remote server, first data and a first sharing key acquired from a patient medical device via a first processor associated with a first medical practice, wherein the first processor is part of a patient system of the first medical practice and which stores various types of information for patients cared for by the first medical practice;

storing, by the remote server, the first data and the first sharing key to a first location of a memory of the remote server;

receiving, at the remote server, second data and a second sharing key acquired from the patient medical device via a second processor associated with a second medical practice, wherein the second processor is part of a second patient system of the second medical and which stores various types of information for patients cared for by the second medical practice;

storing, by the remote server, the second data and the second sharing key to a second location of the memory of the remote server, the second location being different from the first location, wherein the first and second medical practices are legally unaffiliated such that the first patient system is distinct from and unavailable to the second patient system;

comparing, by the remote server, the first sharing key to the second sharing key;

granting, to the first and second processors by the remote server, access to the first and second data stored in the remote server in response to a successful comparison of the first and second sharing keys by remote server as part of the step of comparing; and automatically sharing, by the remote server, the first and second data with both of the first and second processors in response to the grant of access during the step of granting.

20. The method of claim 19, comprising, in response to the successful comparison of the first and second sharing keys:

granting, to the first and second processors by the remote server, access to one or both of previous data and future data uploaded by the first and second processors to the remote server; and sharing, by the remote server, the first data, the second data, and one or both of the previous data and the future data with the first and second processors in response to the grant of access.

* * * * *